(12) United States Patent
Gerber et al.

(10) Patent No.: US 9,622,737 B2
(45) Date of Patent: Apr. 18, 2017

(54) ANCHOR ELEMENT FOR KNOTLESS FIXING OF TISSUE TO A BONE

(71) Applicants: Karl Storz GmbH & Co. KG, Tuttlingen (DE); Universität Zürich, Zürich (CH)

(72) Inventors: Christian Gerber, Zumikon (CH); Dominik Meyer, Zurich (CH); Sascha Berberich, Tuttlingen (DE)

(73) Assignees: Karl Storz GmbH & Co. KG, Tuttlingen (DE); Universität Zürich, Zurich (CH)

( * ) Notice: Subject to any disclaimer, the term of this patent is extended or adjusted under 35 U.S.C. 154(b) by 0 days.

(21) Appl. No.: 14/249,743

(22) Filed: Apr. 10, 2014

(65) Prior Publication Data

US 2014/0222072 A1    Aug. 7, 2014

Related U.S. Application Data

(62) Division of application No. 11/679,446, filed on Feb. 27, 2007.

(30) Foreign Application Priority Data

Feb. 27, 2006    (DE) .................. 10 2006 010 116

(51) Int. Cl.
*A61B 17/04*    (2006.01)

(52) U.S. Cl.
CPC ...... *A61B 17/0401* (2013.01); *A61B 17/0487* (2013.01); *A61B 2017/045* (2013.01); *A61B 2017/0409* (2013.01); *A61B 2017/0412* (2013.01); *A61B 2017/0414* (2013.01); *A61B 2017/0427* (2013.01); *A61B 2017/0438* (2013.01); *A61B 2017/0446* (2013.01); *A61B 2017/0448* (2013.01); *A61B 2017/0453* (2013.01); *A61B 2017/0454* (2013.01)

(58) Field of Classification Search
CPC ....... B25B 15/007; B25B 15/00; B25B 15/06; B25B 19/00; B25B 23/0064; A61B 2017/0409; A61B 2017/0445; A61B 2017/0446; A61B 2017/0448; A61B 2017/0458; A61B 2017/0412; A61B 2017/0427; A61B 2017/0414; A61B 2017/0453; A61B 17/0401
USPC ....... 606/232, 104, 916, 328, 323, 322, 321, 606/310, 304, 300, 302; 411/473, 94, 411/93.6; 81/177.85, 429
See application file for complete search history.

(56) References Cited

U.S. PATENT DOCUMENTS

| | | | | |
|---|---|---|---|---|
| 1,644,074 | A | * | 10/1927 | Morgan .......................... 81/462 |
| 4,296,656 | A | * | 10/1981 | Ernst ................................ 81/429 |
| 5,012,708 | A | * | 5/1991 | Martindell ...................... 81/429 |
| 5,100,417 | A | * | 3/1992 | Cerier et al. .................. 606/139 |

(Continued)

*Primary Examiner* — Christopher L Templeton
(74) *Attorney, Agent, or Firm* — Whitmyer IP Group LLC (57) ABSTRACT

An anchor element serves for knotless fixing of a tissue to a bone by at least one suture threaded through the anchor element. A body of that anchor element has an outer surface with projections. A transverse bore is arranged in a distal end section of the body for receiving a threading passing therethrough. A clamp element serves for clamping the suture threaded transversely through the bore. The clamping element has a portion arranged within the body and is movable within the body towards that transverse bore.

9 Claims, 4 Drawing Sheets

(56) References Cited

U.S. PATENT DOCUMENTS

| | | | |
|---|---|---|---|
| 5,101,698 A * | 4/1992 | Paradiso | 81/451 |
| 5,182,973 A * | 2/1993 | Martindell | 81/429 |
| D350,685 S * | 9/1994 | Perkins et al. | D8/86 |
| 5,957,953 A * | 9/1999 | DiPoto et al. | 606/232 |
| 5,993,458 A * | 11/1999 | Vaitekunas et al. | 606/104 |
| 6,086,608 A * | 7/2000 | Ek et al. | 606/232 |
| 6,436,142 B1 * | 8/2002 | Paes et al. | 623/17.15 |
| 7,172,595 B1 * | 2/2007 | Goble | 606/86 A |
| 8,663,280 B2 * | 3/2014 | Kaplan | 606/232 |
| 8,733,216 B1 * | 5/2014 | Cantlon | 81/439 |
| 2004/0245932 A1 * | 12/2004 | Durand | 315/5.14 |
| 2007/0034060 A1 * | 2/2007 | McCracken | 81/429 |
| 2008/0147063 A1 * | 6/2008 | Cauldwell et al. | 606/60 |
| 2009/0112270 A1 * | 4/2009 | Lunn et al. | 606/301 |
| 2009/0157124 A1 * | 6/2009 | Ferragamo et al. | 606/301 |
| 2010/0224038 A1 * | 9/2010 | Evatt | 81/429 |
| 2011/0112576 A1 * | 5/2011 | Nguyen et al. | 606/232 |

* cited by examiner

ANCHOR ELEMENT FOR KNOTLESS FIXING OF TISSUE TO A BONE

BACKGROUND OF THE INVENTION

The invention relates to an anchor element for knotless fixing of tissue to a bone by means of at least one suture threaded through the anchor element.

Generally, such anchor elements, also called suture anchors, are used in the medical field to ensure that tissues, mostly tendons, that have become detached from a bone can be fixed back onto the bone.

For this purpose, the anchor element and a suture connected to the anchor element are driven firmly into the bone. The protruding suture ends are connected to the detached tissue, by which means the detached tissue is fixed to the bone.

In a first operating technique, known in particular from U.S. Pat. No. 5,690,676, the anchor element is designed such that it has an approximately cylindrical body on whose outer face there are projections that prevent removal of the anchor element after it has been inserted into the bone. These projections can be designed as barb-like elements, for example if the anchor element is driven into the bone, or they can also be designed as an outer thread if the anchor element is turned into the bone in the manner of a screw. The suture is threaded through the transverse bore extending through the body, and the two suture ends are placed in outer longitudinal grooves on the body and guided in the proximal direction. A device called a driver is engaged on the proximal end of the anchor element, and it is usually mounted onto the proximal end of the anchor element. The two suture ends are guided along the driver device and are wound there onto radially projecting stubs for the driving-in procedure.

After the anchor element has been driven into the bone and the driver device has been removed, the two free suture ends are used to secure the detached tissue. To do so, the two suture ends are knotted onto the detached tissue, for example a tendon, lying closely on the bone.

The anchor element anchored in the bone, and the bone itself, form the force/abutment points between which the tissue is fixed.

A disadvantage of this operating technique is that the knotting requires considerable experience and dexterity on the part of the operating surgeon. Such knots can come undone, or soft-tissue bridges can form around the knot because the knot is arranged on the outside of the operating site.

In a development of this operating technique, so-called knotless anchors were developed, which are known for example from US 2004/0138706 A1 and which form the subject matter of the present invention.

This anchor element has a body on whose outer face there are projections that prevent removal of the anchor element inserted in the bone. A transverse bore is arranged in the distal end area of the body and extends through the latter. A suture is threaded transversely through the body. A clamp element is provided which is moveable along the body and is used to clamp the suture. The clamp element is designed as an outer axially moveable sleeve.

In this operating technique too, the suture is first threaded through the anchor element. One of the free suture ends is pushed, mostly with the aid of a needle, through the tissue to be fixed, and the pushed-through end is then threaded back in the opposite direction through the transverse bore in the anchor element. The connection between the anchor element and the tissue to be fixed takes the form of a suture loop. The anchor element can now be introduced into the bone, together with the suture after which the free suture ends are pulled so that the protruding loop of the suture, connected to the tissue, is drawn toward the fixing location.

The relative position between the suture and tissue connected to it, and the anchor element is now fixed not by forming a knot, but instead by moving a clamp element through which the suture is fixed or as it were clamped in a defined position on the anchor element. In this way, the loop holding the tissue is also fixed. The protruding free ends can then be cut off, for example, and there is no need to apply a knot.

In the US 2004/0138706 A1, the clamp element is designed as a sleeve which is mounted on the outside of the body of the anchor element. The sleeve and body are displaceable relative to one another.

In one position of displacement of the sleeve, the suture threaded through the body is freely movable, for example so that the tissue pierced by the suture can be drawn onto the bone and fixed in its position. The sleeve is then moved in order to clamp the suture and fix it in its relative position.

As can be seen in particular from moving from FIG. 4 to FIG. 5 of US 2004/0138706 A1, there are several relatively sharp-edged clamp points between which the suture is squeezed. This results in relatively high shearing forces, which means that damage to the suture, and therefore tearing-off of the suture, cannot reliably be ruled out.

In addition, the outer sleeve is a very complicated structural part which, in order to exert a clamping force, has to be slightly spread open by the anchor element. For this purpose, suitable lock-type bridges are needed between the outer face of the body of the anchor element and the inner face of the sleeve, which make release from this locked position difficult or impossible. For this reason, corrective measures, for example during temporary release of the clamping connection, can only be carried out with difficulty, if at all.

It should be borne in mind that the dimensions of such clamp elements involve lengths in the range of several centimeters and diameters of several millimeters.

Therefore, not only is the production of such parts extremely complex, their handling is also very difficult and, in particular, their stability in respect of the holding or fixing force is extremely problematic.

If a tendon subjected to high loading, for example a tendon from the shoulder area or the knee area, is fixed, it is evident that considerable tensile forces from the tendon act on the assembled structure introduced into the bone and composed of body, clamp element and clamped suture.

If one considers the aforementioned dimensions, it will be evident that the wall thickness of the outer sleeve may at best be in the range of fractions of millimeters, although it is this structural part that is intended to provide the clamping force for holding the suture.

Since the sleeve, because of its construction, covers a certain proportion of the outer face of the body of the anchor element, but this anchor element serves to hold the whole assembly in the bone via the projections present on its outer face, suitable structural measures have to be taken to ensure that the body of the anchor element as such can in fact be safely anchored in the bone.

This leads to additional and considerable outlay in terms of construction.

It is an object of the present invention to provide an anchor element for knotless fixing a tissue, which is of simple construction, ensures effective anchoring of the anchor element and, at the same time, allows the suture to be fixed efficiently and without damaging it.

SUMMARY OF THE INVENTION

The object is achieved by an anchor element having a body with an outer surface, which has projections projecting from said outer face for preventing removal of said anchor element when inserted in a bone. A transverse bore is arranged in a distal end section of said body, said transverse bore extending through that body. The transverse bore serves for threading said at least one suture transversely through that body A clamp element is provided for clamping said suture threaded transversely through said bore. Said clamping element having a portion arranged within said body, said clamping element being arranged moveable within said body and being moveable towards said transverse bore for clamping said suture in said transverse bore.

An important advantage of arranging a portion of the displaceable clamp element in the inside of the body is that the outside of the body is not covered by this clamp element, such that the outside of the body of the clamp element is available fully for anchoring to the bone. When the portion of the clamp element arranged in the inside is moved away from the transverse bore, the suture threaded through the transverse bore can be freely moved. By moving the inner portion of the clamp element in the direction of the transverse bore, the portion of the suture received in the transverse bore can then be clamped.

This can be done directly by the clamp element itself, or the clamp element can squeeze a further element, for example a clamping aid received in the transverse bore. Since the outside of the anchor element does not have to be covered during these movements, these maneuvers can be performed in the inside of the body after the anchor element has already been driven into the bone. In this way, it is also possible, for example, to correct the lie of the suture when the anchor element is already inserted, without the anchor element as such having to be moved relative to the bone for this purpose.

The maneuvering of the clamp element in the inside of the body can be done from the proximal end of the anchor element, for which purpose the clamp element could also protrude at the proximal end. As regards its outer structural features, the body of the anchor element can be constructed exactly like an anchor element that works with knotting. The inside of the body simply has to be provided with a suitable cavity, which is very easy to produce and into which the inner portion of the clamp element can be introduced. This inner portion of the clamp element can be made solid in order to be able to exert the sufficient clamping force on the suture received in the transverse bore.

The existing inner wall of the transverse bore is available as an abutment for the clamping by the clamp element. This wall provides the suture with a sufficiently large contact surface on which the suture to be clamped can be applied or fixed by the displaced clamp element. In other words, the suture can wedge itself on the inner wall of the transverse bore, such that the clamping forces are distributed over a relatively large surface area, with the result that the danger of damage and shearing of the suture is greatly reduced.

In an embodiment of the invention, the body of the anchor element has an axially extending inner bore for receiving said clamping element.

This measure allows to securely receive at least said portion of the clamping element arranged within the axially extending inner bore.

In a further embodiment of the invention said inner bore opens into said transverse bore.

This measure has the advantage that the portion of the clamping element arranged within the body can be guided securely into the transverse bore for clamping the suture therein.

In another embodiment of the invention, a distal end of the clamp element is rounded.

This measure has the advantage that the aforementioned pressing on the suture in the transverse opening can be exerted with low shear force and without damaging the suture.

In a further embodiment of the invention, a gentle hollow is provided in said transverse bore opposite to said rounded distal end of said clamping element. The gentle hollow approximately corresponds to the rounded distal end.

This method has advantage that parts of the suture can be pressed or squeezed into the gentle hollow enhancing the clamping of the suture between clamping element and transverse bore.

In another embodiment of the invention, the portion of the clamp element arranged inside the body is designed as a pin.

This measure has the advantage that this geometry permits a compact, stable clamp element which is able to transmit the necessary clamping force, even when the overall dimensions of the anchor element are very small.

In another embodiment of the invention, the pin is designed as a headless screw.

This measure has the advantage that a very compact clamp element is provided which is easy to control and which, by simple turning, can be moved to and fro within the body of the anchor element.

In another embodiment of the invention, the clamp element is received completely in the body.

This measure has the considerable advantage that the outer contour of the anchor element is not in any way impaired by the provision of the clamp element, that is to say the entire outer contour of the anchor element can be used for the actual function, namely that of anchoring in the bone. Seen from the outside, an anchor element according to the invention can appear, structurally, like an anchor element of the kind known for example from U.S. Pat. No. 5,690,676, but now used in the knottless technique. With the latter, there is already sufficient experience regarding the structural designs that provide a sufficient anchoring force, and this wealth of experience can be exploited here.

In another embodiment of the invention, the clamp element is designed as a conical element.

This measure has the advantage that such an element is very easy to produce and simply has to be driven forward in the inside of the body in order to fix the suture. By suitable choice of the cone angle and of the length of the inner portion, the sufficient holding force or clamping force can be exerted.

In another embodiment of the invention, the clamp element has an assembly feature onto which a tool of a driver device for the anchor element can be attached.

This measure then has the considerable advantage that the same tool with which the anchor element is driven in can also be used to control the clamp element, in other words to move it in the direction of the transverse bore for clamping the suture.

As regards production and handling, this measure has the advantage that it is not necessary to provide two tools, one for driving in the anchor and one for moving the clamp element. The insertion of the anchor element and the displacement of the clamp element can be carried out in succession using one tool.

This is especially of help to the operating surgeon and facilitates this operating technique.

The materials used for the structural elements can, depending on the requirements, be metals, in particular titanium, or said structural elements can be made of bioabsorbable materials, if so desired.

It will be appreciated that the aforementioned features and the features still to be explained below can be used not only in the cited combinations, but also in other combinations or singly, without departing from the scope of the present invention.

BRIEF DESCRIPTION OF THE DRAWINGS

The invention is described and explained in more detail below on the basis of a number of selected illustrative embodiments and with reference to the attached drawings, in which.

DETAILED DESCRIPTION OF PREFERRED EMBODIMENTS

An anchor element shown in FIGS. 1 to 4 is designated in its entirety by reference number 10.

Figure 1:
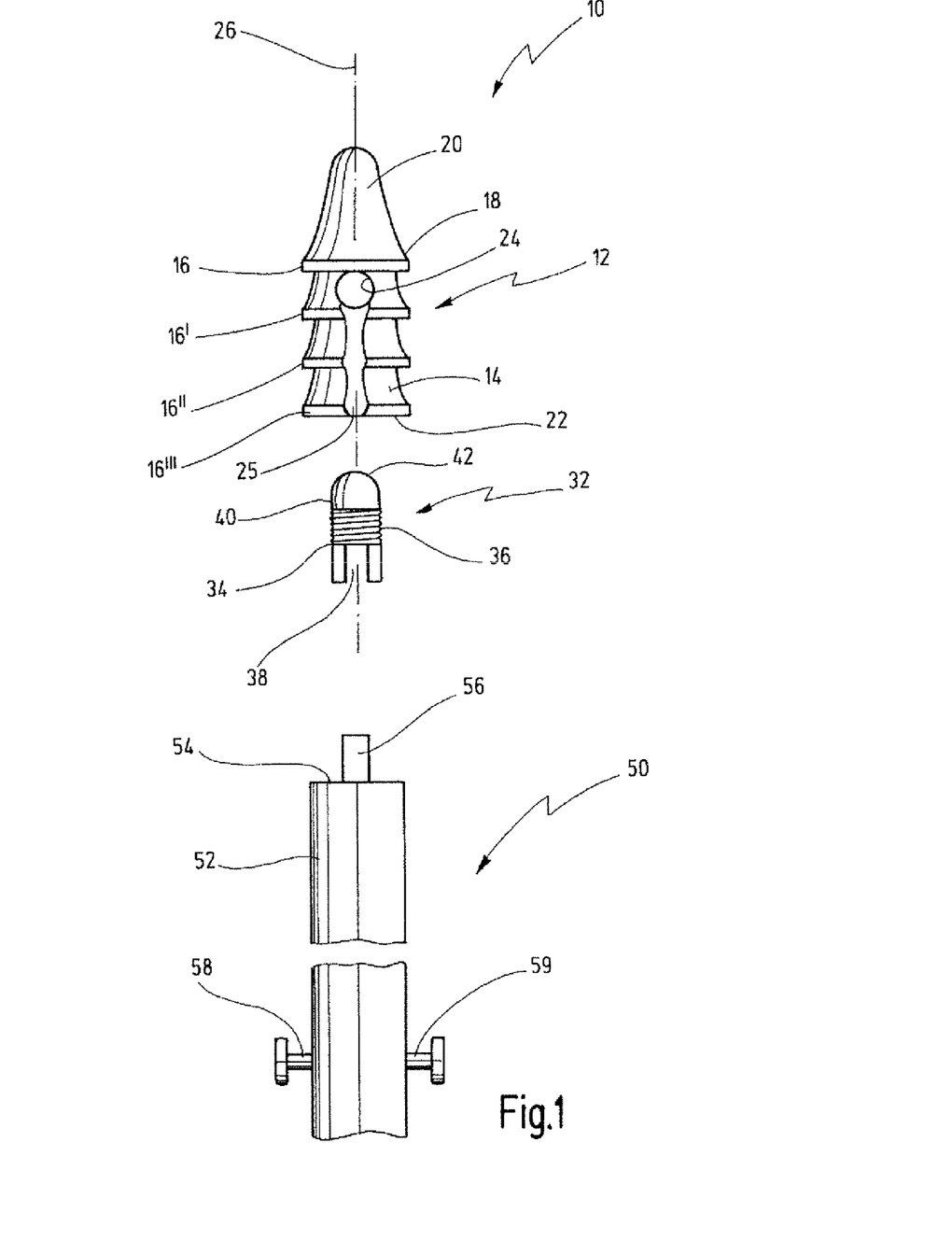
FIG. 1 shows an exploded view of an anchor element according to the invention and its clamp element, and with the maneuvering tool for fitting the anchor element into the bone being depicted at the lower end.

The anchor element 10 has an elongate, roughly cylindrical body 12 from whose outer face 14 a number of projections 16 to 16''' protrude. The projections 16 to 16''' are designed as protruding annular flanges which, viewed in the distal direction, each merge with the next annular flange via approximately conically tapering portions. A distal end area 18 of the body 12 is provided with a rounded tip 20. A proximal end 22 is formed by the cross-sectional surface area of the last projection 16'''.

In the distal end area 18 of the body 12, a transverse bore 24 is arranged extending through the latter. Starting from the mouth of the transverse bore 24, two diametrically opposite longitudinal grooves 25, cut into the projections 16' to 16''', extend proximally along the longitudinal axis 26 of the body 12.

Figure 2:
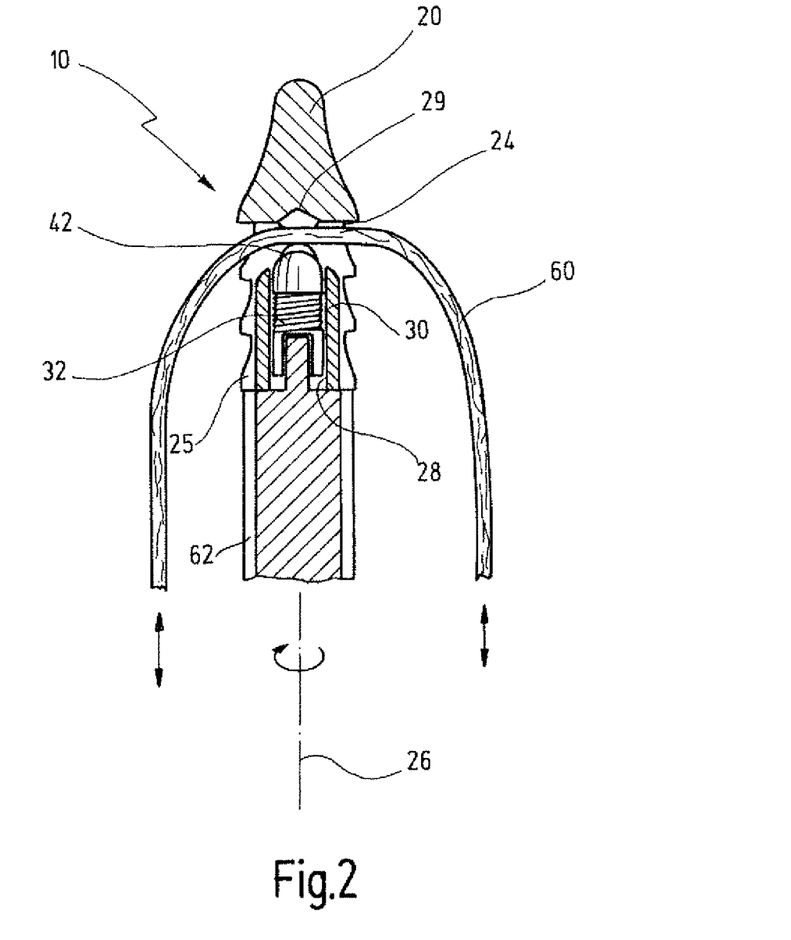
FIG. 2 shows a longitudinal section through the anchor element from FIG. 1 with the clamp element inserted, with the maneuvering tool applied, and with a suture threaded through the anchor element but still freely movable.

The transverse bore is used for threading a suture 60 through the body 12, as shown in FIG. 2. The suture portions protruding from both ends of the transverse bore 24 can be placed into the longitudinal grooves 25, such that these suture portions can be guided proximally from the direction of the transverse bore 24 while bearing closely on the body 12.

From the proximal direction, an axial bore 28 is formed centrally within the body 12 (see FIG. 2) and opens at the distal end into the transverse bore 24.

An inner thread 30 is cut in the axial bore 28.

This axial bore 28 is used for receiving a clamp element 32.

The clamp element 32 is composed of a pin 34 on whose outer face there is an outer thread 36, which meshes with the inner thread 30 of the axial bore 28.

Formed at the proximal end of the pin 34, there is a recess 38, here in the form of a diametrical incision, whose purpose will be explained below. At the distal end 40, the clamp element 32 is provided with a rounded part 42. With that design, the pin 34 is a headless screw.

A device referred to as a driver 50, with which the anchor element 10 is maneuvered, is shown at the bottom end of FIG. 1.

The driver device 50 comprises a rod 52 from whose distal end face 54 a tool 56 projects which is designed such that it can be inserted with a form-fit into the recess 38 of the clamp element 32. The end face 54 of the driver device 50 is moreover designed such that it can be placed on the proximal end 22 of the body 12 of the anchor element 10.

At a distance axially from its end face 54, the driver device 50 is provided with two diametrically protruding stubs 58, 59 around which the two protruding suture ends can be wound. At the proximal end, the rod 52 ends in a handpiece (not shown here) via which the driver device 50 can be gripped by hand by the person operating it.

FIG. 2 now shows a situation in which the clamp element 32 is received in the inside of the body 12, with the outer thread 36 inserted into the inner thread 30, specifically such that the suture 60 guided through the transverse bore 24 is freely movable, as indicated by the double arrows.

The proximal end 22 of the body 12 sits on the end face 54 of the driver device 50, of which the tool 56 engages in the recess 38 of the clamp element 32.

As has been mentioned above, the longitudinal grooves 25 on the outer face 14 of the body 12 allow the suture ends to be guided in the proximal direction while bearing closely on the body 12. Correspondingly, grooves 62 are cut into the rod 52 of the driver device 50 in order to guide these suture ends as far as the diametrically protruding stubs 58, 59 around which they are wound.

Figure 4:
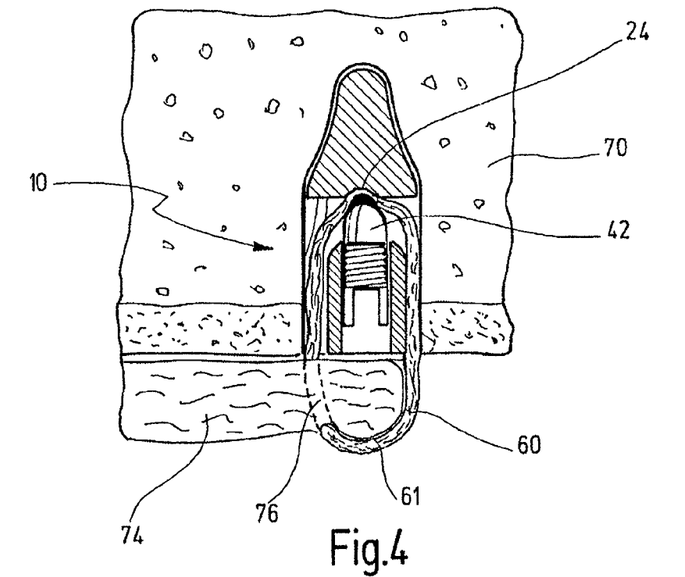
FIG. 4 shows a cross section after the anchor element has been fitted and the tendon has been fixed by means of the suture, and the suture has been fixed in the bone by means of the clamp element.

As will be evident in particular from the cross-sectional view in FIG. 2, turning the driver device 50 about the longitudinal axis 26 of the assembled structure causes the clamp element 32 to turn in the inside of the anchor element 10, as a result of which the clamp element 32 is moved in the direction toward the transverse bore 24 and into the latter. Referring to FIGS. 2 and 4, the tool 56 of the driver device 50 and the recess 38 in the clamp element 32 are configured so as to provide rotational engagement therebetween, while allowing for relative axial movement therebetween when the end face 54 of the driver device 50 rests on the proximal end 22 of the body 12 of the anchor element 10. When the end face 54 of the driver device 50 rests on the proximal end 22 of the body 12 of the anchor element 10, rotation of the tool 56 of the driver device 50 causes rotation of clamp element 32 and, consequently, axial movement of the clamp element 32 within the axial bore 28 of the anchor element 10. The portion of the suture 60 received in the transverse bore 24 is applied, by the rounded part 42, against the opposite inner wall of the transverse bore 24 and, when driven further forward, correspondingly clamped.

By means of the round and gentle profile of the rounded part 42 of the clamp element 32 and the corresponding profile of the inner wall of the transverse bore 24, the clamping force on the suture can be distributed across a relatively large surface area, as a result of which a squeezing or shearing off of the fixed suture 60 in the transverse bore 24 can be avoided.

It will be evident from the cross-sectional view in FIG. 2 that, on the distal side of the transverse bore 24, the axial bore 28 is continued in the form of a gentle hollow 29 which corresponds approximately to the contour of the rounded part 42, such that the suture 60 can be fixed particularly gently, but still securely between hollow 29 and rounded part 42.

As will be seen from FIG. 2, the anchor element 10 bearing on the end face 54 of the driver device 50 can be driven into a bone by means of the latter, for example with a hammer.

The length of the tool 56 and the depth of the recess 38 in the clamp element 32 are chosen such that the clamp element 32 is not damaged in this process, but such that there is sufficient engagement between these two structural elements to be able to subsequently turn the clamp element 32 and thus produce the clamping action.

Figure 3:
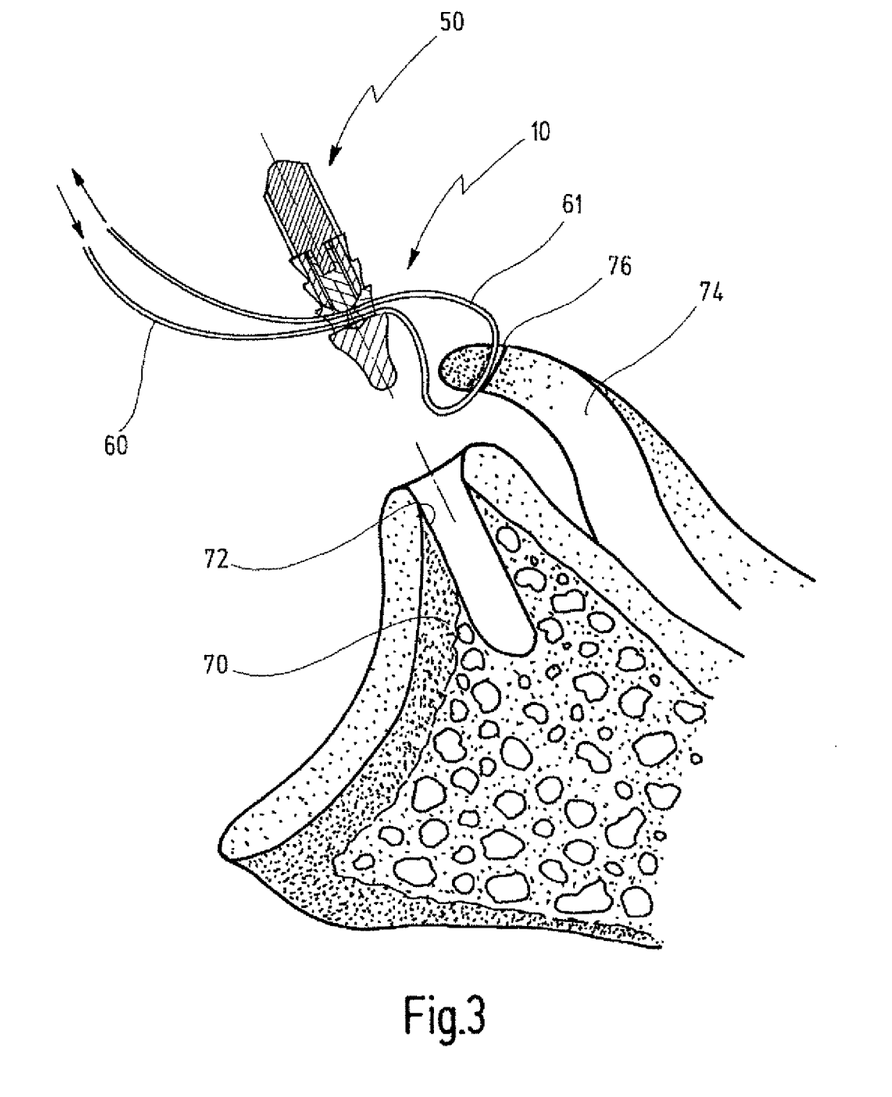
FIG. 3 shows a snapshot of the operating technique for fitting the anchor element, in which view the assembly shown in FIG. 2 can be seen, with the threaded suture having already been connected to a tissue and having been threaded back through the transverse bore.

FIG. 3 shows a snapshot of an operating technique in which an anchor element 10 according to the invention is fitted.

Part of a tissue 74, for example a tendon, has become detached from a bone 70 and is now to be fixed back onto the bone 70.

In the illustrative embodiment shown, an opening 72, for example a bore, has been formed in the bone 70 in the area of tissue detachment, the internal diameter of the opening 72 being slightly smaller than the external diameter of the projections 16 on the body 12 of the anchor element 10. The assembly made up of the anchor element 10, and clamp element 32 received therein, and of the driver device 50 is brought to the operating site, and the suture 60 is threaded once through the transverse bore 24, as shown in FIG. 2. One of the free ends is pushed, if appropriate with the aid of a needle, through a detached portion of the tissue 74, the resulting cut 76 being shown in cross section in FIG. 3. The suture portion emerging through the cut 76 is guided once again through the transverse bore 24, specifically in the opposite direction to the previous one.

As can be seen from FIG. 3, this creates a loop 61 via which the tissue 74 is connected to the clamp element 10. The two free suture ends are now guided closely along the surface of the structure composed of driver device 50 and anchor element 10 to the stubs 58, 59 and are threaded around these.

The anchor element 10 is then driven into the opening 72 of the bone 70 by means of the driver device 50. By pulling on the free ends of the suture 60, the detached tissue portion 74 can be brought into the desired position relative to the bone and to the anchor element. By turning the driver device 50, the clamp element 32 is now moved into the transverse bore 24 and clamps the two suture portions received in the transverse bore. The driver device 50 is removed, and the protruding suture portions can be cut off.

It is still entirely possible here to make certain corrections to the lie of the suture, even with the anchor element 10 already fitted, by means of slightly loosening the clamp element 32 again. After the driver device 50 has been removed, the tissue 74 to be fixed lies once again on the bone 70, as shown in FIG. 4. Only the loop 61 of the suture 60 is visible, and there is therefore no bulky knot. In the inside of the body 12, the portions of the suture 60 received in the transverse bore 24 are fixed in position by the rotated clamp element 32.

What is claimed is:

1. An anchor system for knotless fixing of a tissue to a bone, said anchor system comprising
   an anchor element comprising:
      a body having an outer face,
      projections projecting from said outer face for preventing removal of said anchor element when inserted in the bone,
      a distal end section of said body being rounded,
      a proximal end of said body defining a bearing surface,
      a transverse bore arranged in said distal end section of said body, said transverse bore extending through said body, and adapted to receive at least one suture transversely through said body,
      and an axial bore, said axial bore opening into said transverse bore and extending from the proximal end of said body up to said transverse bore, said axial bore having an inner thread;
      said transverse bore and said axial bore being positioned perpendicular to one another;
      an axially extending pin having an outer thread meshing with said inner thread and being housed axially movable in said axial bore, an outer diameter of said pin corresponding to an inner diameter of said axial bore, said pin, when turned in, adapted to move in a direction towards the transverse bore and into the latter, said pin having a distal end configured to clamp the at least one suture against a distal wall of said transverse bore, and said pin having a recess provided in a proximal end thereof; and
   a driver device comprising:
      a proximal end adapted to be manipulated by a user of the anchor system and a distal end engaging said anchor element,
      the distal end of the driver device comprising a shoulder and a pin engagement member projecting distally from said shoulder, the shoulder of the driver device defining a bearing surface configured to mate with the bearing surface of said anchor element such that axial force exerted on the proximal end of the driver device is transmitted to the anchor element through the shoulder of the driver device, and
      the pin engagement member of said driver device and the recess of said pin being configured so as to provide rotational engagement therebetween, while allowing for relative axial movement therebetween when said shoulder rests on said bearing surface of said anchor element, such that, when said shoulder rests on said bearing surface of said anchor element, rotation of the pin engagement member of said driver device causes rotation of said pin and, consequently, axial movement of said pin within the axial bore of said anchor element,
      whereby the driver device is adapted to be used for both insertion of the anchor element into the bone and also clamping of the at least one suture inserted through the transverse bore.

2. The anchor system of claim 1, wherein said distal end of said pin is rounded.

3. The anchor system of claim 2, wherein opposite to said rounded distal end of said pin, a gentle hollow is provided in said transverse bore, said gentle hollow approximately corresponds to said rounded distal end of said pin.

4. The anchor system of claim 1, wherein said pin is designed as a headless screw.

5. The anchor system of claim 1, wherein the pin engagement member of said driver device and the recess of said pin are configured so as to provide direct engagement therebetween during said rotational engagement therebetween.

6. The anchor system of claim 1, wherein the pin engagement member of said driver device and the recess of said pin are configured such that rotation of the pin engagement member of said driver device causes rotation of said pin within the axial bore and, consequently, axial movement of said pin within the axial bore of said anchor element.

7. An anchor system for knotless fixing of a tissue to a bone, said anchor system comprising:
- an anchor element comprising:
  - a body having an outer face,
  - projections projecting from said outer face for preventing removal of said anchor element when inserted in the bone,
  - a distal end section of said body being rounded,
- a proximal end of said body defining a bearing surface,
  - a transverse bore arranged in said distal end section of said body, said transverse bore extending through said body, and adapted to receive at least one suture transversely through said body,
  - and an axial bore, said axial bore opening into said transverse bore and extending from the proximal end of said body up to said transverse bore, said axial bore having an inner thread;
  - said transverse bore and said axial bore being positioned perpendicular to one another;
  - a clamping element having an outer thread meshing with said inner thread and being housed axially movable in said axial bore, an outer diameter of said clamping element corresponding to an inner diameter of said axial bore, said clamping element, when turned in, adapted to move in a direction towards the transverse bore and into the latter, said clamping element having a distal end configured to clamp the at least one suture against a distal wall of said transverse bore, and said clamping element having a recess provided in a proximal end thereof; and
- a driver device comprising:
  - a proximal end adapted to be manipulated by a user of the anchor system and a distal end engaging said anchor element,
  - the distal end of the driver device comprising a shoulder and a clamping element engagement member projecting distally from said shoulder, the shoulder of the driver device defining a bearing surface configured to mate with the bearing surface of said anchor element such that axial force exerted on the proximal end of the driver device is transmitted to the anchor element through the shoulder of the driver device, and
- the clamping element engagement member of said driver device and the recess of said clamping element being configured so as to provide rotational engagement therebetween, while allowing for relative axial movement therebetween when said shoulder rests on said bearing surface of said anchor element, such that, when said shoulder rests on said bearing surface of said anchor element, rotation of the clamping element engagement member of said driver device causes rotation of said clamping element and, consequently, axial movement of said clamping element within the axial bore of said anchor element,
- whereby the driver device is adapted to be used for both insertion of the anchor element into the bone and also clamping of the at least one suture inserted through the transverse bore.

8. The anchor system of claim 7, wherein the clamping element engagement member of said driver device and the recess of said clamping element are configured so as to provide direct engagement therebetween during said rotational engagement therebetween.

9. The anchor system of claim 7, wherein the clamping element engagement member of said driver device and the recess of said clamping element are configured such that rotation of the clamping element engagement member of said driver device causes rotation of said clamping element within the axial bore and, consequently, axial movement of said clamping element within the axial bore of said anchor element.

* * * * *